United States Patent [19]

Steinbruegge et al.

[11] Patent Number: 4,490,845
[45] Date of Patent: Dec. 25, 1984

[54] AUTOMATED ACOUSTO-OPTIC INFRARED ANALYZER SYSTEM

[75] Inventors: Kenneth B. Steinbruegge, Murrysville; Milton S. Gottlieb, Churchill, both of Pa.

[73] Assignee: Westinghouse Electric Corp., Pittsburgh, Pa.

[21] Appl. No.: 345,123

[22] Filed: Feb. 2, 1982

[51] Int. Cl.³ .............................................. G01J 3/32
[52] U.S. Cl. ........................................ 382/1; 250/339
[58] Field of Search ............... 250/341, 338, 340, 345, 250/339; 356/51

[56] References Cited

U.S. PATENT DOCUMENTS

| | | | |
|---|---|---|---|
| 3,939,348 | 2/1976 | Barrett | 250/340 |
| 3,987,304 | 10/1976 | Kreuzer | 250/340 |
| 4,191,967 | 3/1980 | Dansac et al. | 358/113 |

OTHER PUBLICATIONS

Chang, I. C., "Laser Detection Utilizing Tunable Acoustooptic Filter", *IEEE Journal of Quantum Electronics*, vol. QE14, No. 2, 2/78.
Harris, S. E., and R. W. Wallace, "Acousto—Optic Tunable Filter", *Journal of the Optical Society of America*, vol. 59, No. 6, Jun. 1969.
Steinbrugge, Gottlieb and Feichtner, "Automated Acousto—Optic Tunable Filter (AOTF) Infrared Analyzer", SPIE, vol. 268, Imaging Spectroscopy, (1981), pp. 160–166.
Dixon, R. W., IEEE J. Quantum Elec., QE-3, 85, (1967).
"Acousto—Optic Properties of Some Chalcongenide Crystals", J. Appl. Physics, 45, 5154, (1974).
Conroy, J. J. et al., "Recent Developments in Infrared AOTFs", Proceedings SPIE, 202, 33, (1979).

*Primary Examiner*—John C. Martin
*Assistant Examiner*—Erin A. McDowell
*Attorney, Agent, or Firm*—W. G. Sutcliff

[57] ABSTRACT

An automated acousto-optic tunable filter infrared analyzer system useable in a variety of industrial and commercial control applications. The system relies upon a narrow band pass tunable acousto-optic filter which is selectively tuned by predetermined rf frequency signals to selectively transmit the narrow band pass of interest which corresponds to a specific molecular species for identification and analysis. The system includes a microcomputer and associated memory function to measure and compare detected signals from an infrared detector which converts the filtered infrared signal to an electrical signal. The memory provides control signals for the computer and for controlling the sequence and frequency of rf energy applied to tune the filter. In this way, the near to mid range infrared can be analyzed for absorption bands corresponding to predetermined molecular species such as combustion product gases, and a feedback signal generated to control the combustion process.

8 Claims, 1 Drawing Figure

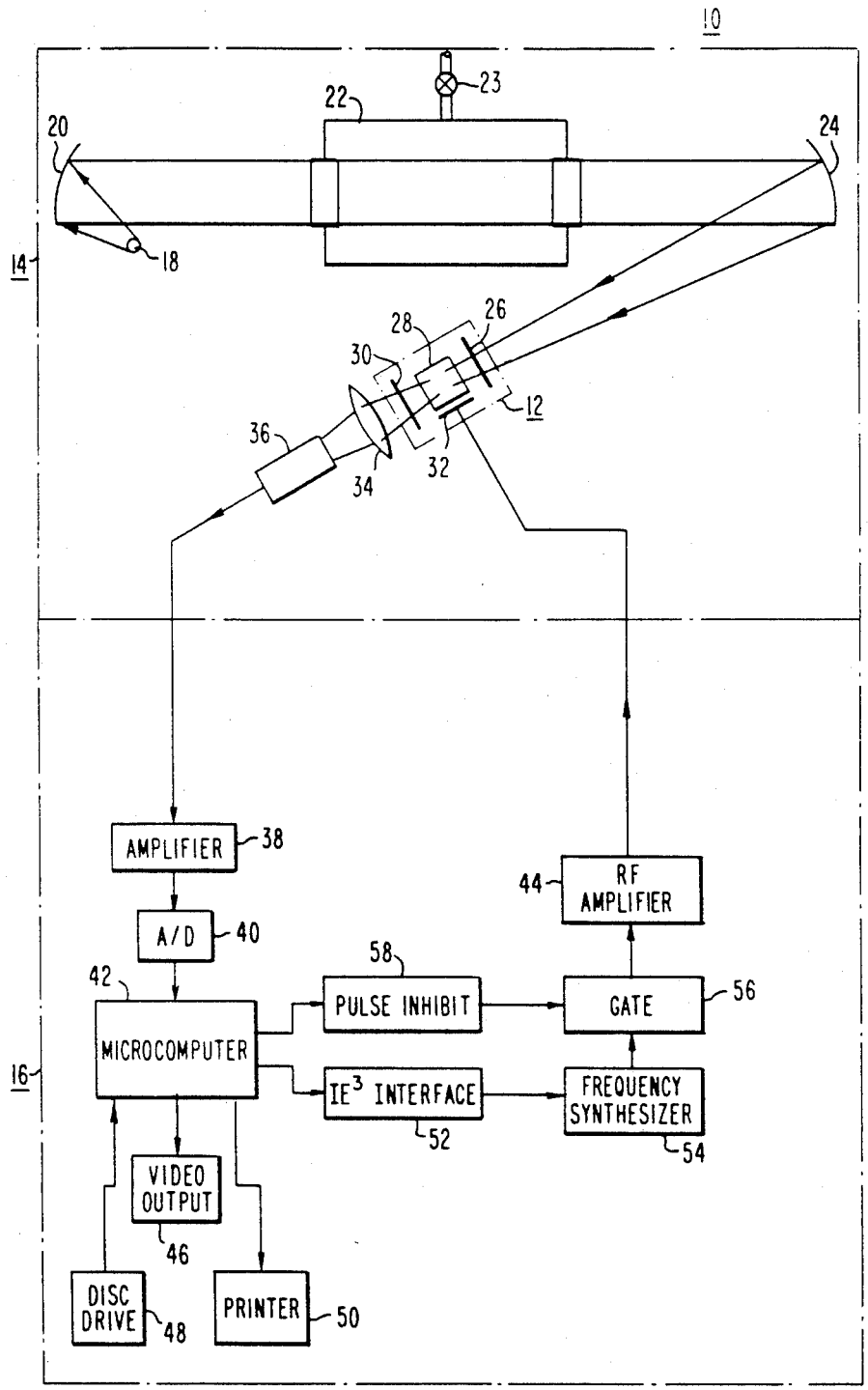

AUTOMATED ACOUSTO-OPTIC INFRARED ANALYZER SYSTEM

BACKGROUND OF THE INVENTION

The present invention relates to infrared analyzers which can be used in a variety of industrial and commercial applications. In particular the present invention utilizes an acousto-optic tunable filter which is operable in the near and mid-infrared spectral regions, which permits construction of a compact-high-throughput infrared spectral analyzer controlled by a microcomputer.

A large and growing market exists for analytical devices which can be used to analyze reaction products of a wide variety of industrial processes. In addition on-line real time combustion product analyzers are needed to facilitate more efficient burning of hydrocarbon fuels. Multi-function combustion product analyzers are needed to keep track of combustion emission and to ensure that the emission is within the limits set by environmental legislation. On-line multifunction analyzers are needed in the chemical and petroleum industries to function as process analyzers to facilitate process control systems. The petroleum industry as well as the emerging synthetic fuel industry has need for compact stable, simple analytical instruments for determining hydrocarbon fractions.

The analytical devices to date utilize ultraviolet and infrared spectrophotometry, as well as gas and liquid chromatography in meeting the laboratory and industrial needs outlined above. Such optical instruments as well as the system of the present invention utilize the following important characteristics of materials. A particular molecule has a characteristic absorption spectrum which is dissimilar from that of all other molecules. The spectra of mixtures of molecules are additive and the absorption is proportional to the concentrations of the molecules. Optical absorption spectra can be obtained from any type of sample be it solid, liquid, or gas so long as the sample is optically transmissive, and the spectra can be obtained in a non-destructive testing of the sample.

Infrared radiation is particularly suited for analyzing complex streams of hydrocarbons and combustion products because of the infrared absorption characteristics of the major gases produced in such systems. The existing infrared analytical systems typically are limited to measuring a single wavelength of interest at a given time. Such infrared instruments utilize prisms, selectively absorptive filters, or diffraction gradings as the filtering mechanism can require mechanical changing of the optical filter element in order to function over a variety of wavelengths. Such mechanical changeovers require realignment of the systems which are time consuming and difficult to achieve at an on-site location.

It has recently been recognized that certain birefringent optical materials which are termed acoustooptic materials can be used as a filter in a spectrum analyzer. In such acousto-optic materials, a light beam propagating as an E-ray can under certain conditions be converted into an O-ray by interation with, and diffraction from, an acoustic wave propagating from the same medium. This phenomenon has been used in fabricating narrow band optical filters, the peak transmission wavelength of which can be selected by properly choosing the frequency of the acoustic wave. Even more recently, new efficient infrared transmissive acousto-optic materials such as thallium-arsenic-selenide, as described in U.S. Pat. No. 3,792,287 owned by the assignee of the present invention, provide the possibility of operation over the near to mid-infrared spectrum from about 1 micrometer to about 16 micrometers.

SUMMARY OF THE INVENTION

An automated acousto-optic tunable filter infrared analyzer system is detailed which permits rapid electronic tuning of the filter to a selected infrared bandpass via the acousto-optic interaction with infrared radiation passed through a sample. The infrared analyzer system includes means for directing infrared radiation through the sample to be analyzed, which sample has a predetermined infrared absorption characteristic. Means are provided for directing the infrared radiation through an acousto-optic tunable filter after the infrared radiation has passed through the sample species. An acousto-optic tunable filter includes an input polarizer for selectively polarizing the infrared radiation. The tunable filter includes an optically aligned acousto-optic crystal through which the selectively polarized infrared radiation is passed at a predetermined angle relative to the crystal optic axis. An acoustic transducer means is coupled to the crystal and to a variable frequency rf energy source whereby acoustic waves are launched in the crystal to interact with the selected narrow bandwidth portion of the polarized infrared radiation to make it distinguishable from the remaining radiation. The tuned or selected narrow bandwidth infrared radiation is a function of the frequency of the rf energy source, which is connected to the acoustic transducer of the filter. Infrared radiation detection means are coupled to the filter to detect the output filtered infrared radiation to generate an output electrical signal as a function of the output filtered infrared radiation. Automated computing means are provided, with the detection means output electrical signal applied to the computing means for determining the sample species present in the sample. The computing means includes means for selectively actuating the rf energy source to determine the timing and frequency of rf energy applied to the acoustic transducer to thereby determine the selected or filtered narrow bandwidth infrared wavelength of interest.

BRIEF DESCRIPTION OF THE DRAWING

The sole FIGURE is a schematic illustration of an embodiment infrared analyzer system of the present invention.

DESCRIPTION OF THE PREFERRED EMBODIMENT

An automated acousto-optic tunable filter infrared analyzer system 10 is seen in the sold Figure configured from several subsystems and components including an acousto-optic tunable filter 12. The analyzer system 10 can be viewed as having two major subsystems, an optical system 14, and an electronic system 16. The optical system 14 of the analyzer system 10 is essentially an infrared solid-state spectrometer which has been designed to permit operation over a relatively wide spectral range. An infrared radiation source 18 such as a Nernst glower is used as the primary source of broadband infrared radiation for the system. A portion of the output infrared radiation from the source 18 is collected and collimated by mirror 20. The collimated beam from mirror 20 passes through a sample cell 22 which contains the sample species or material to be analyzed. The sample material may be a gas such as methane, carbon dioxide, carbon monoxide, which exhibit narrow band absorption in the infrared and can be introduced to sample cell 22 via valve 23. A second mirror 24 is aligned with the first mirror 20 to collect the collimated beam after it passes through the sample cell 22, with the second mirror 24 directing the beam to the acousto-optic tunable filter 12.

The acousto-optic tunable filter (AOTF) 12 comprises an input polarizer 26, an acousto-optic crystal 28, and an output polarizer 30. The present material of choice for the AOTF crystal is thallium arsenic selenide, $Tl_3AsSe_3$. The input optical face of the crystal 28 is cut so as to be normal to the incident infrared beam, while the output beam is diffracted at an angle of about 6° to the incident beam, and the exit optical face is cut so as to be normal to this diffracted beam. An acoustic transducer 32 is mated to one of the opposed side surfaces of the crystal 28 and consists of an X-cut lithium niobate crystal plate which is efficiently coupled to the acoustic crystal. A conductive electrode pattern is provided on the lithium niobate transducer substrate. This electrode is driven from the rf system which will be described hereafter. The acousto-optic crystal 28 is designed such that the crystalline b-c axes are contained in the optical plane of incidence of the crystal and the optical beam is propagated at a selected angle which for the material described above has been about 21 degrees relative to the crystallographic c or optic axis in early work, and is more typically about 30 degrees but is not critical. The acoustic energy from the transducer 32 is propagated nearly normal to the optical beam propagation direction. When rf power is applied to the transducer the polarized input infrared radiation is propagated along a path at a predetermined angle to the optic axis of the crystal and a narrow pass band frequency selectively interacts with the acoustic wave. The polarization of this selected or tuned optical frequency radiation is rotated 90 degrees from the polarization of the unfiltered beam. This selected or tuned narrow pass band infrared radiation is also distinguishable from the remaining input radiation because it is shifted or diffracted at a small angle relative to the unaffected input radiation path, such as the 6 degree offset described above. Thus the filtered light can be separated either spatially due to this offset angle without use of an output polarizer, or by means of an output polarizer.

The input polarizer 26 and output polarizer 30 both comprise what are termed wire grid polarizers in which a planar plurality of parallel closely-spaced conductors are typically provided upon a radiation transmissive substrate, with the spacing between adjacent conductors being less than the wavelength of transmitted radiation. Such infrared polarizers are available commercially under the product designation IGP228 from Cambridge Physical Sciences. The specific identified wire grid polarizers are operable over the spectral range of about 1 to 12 micrometers with other such polarizers operable over a wider infrared range. The acousto-optic crystal 28 has a base plan which contains the crystalline b-c axes, and the optical beam is propagated at about 21 degrees relative to the crystallographic c or optic axis. This angular relationship between the input radiation beam and the crystalline c or optic axis is not critical and can be varied, but variation will affect the specific rf tuning frequency which is used to filter or tune the desired narrow bandwidth wavelength of interest. The parallel closely-spaced conductors of the input polarizer 26 are aligned with the plane formed by the b-c crystalline axes of the acousto-optic crystal to efficiently polarize the input infrared radiation in a plane parallel to the b-c crystal plane. In the embodiment shown the output polarizer 30 has its spaced conductors disposed transverse to those of the input polarizer, whereby only the 90 degree shifted polarized selected narrow bandwidth portion of the infrared radiation transmitted through the acousto-optic member is passed to an infrared sensitive pyroelectric infrared detector 36 which is operable over a wide spectral range. A focusing lens 34 can be utilized to focus the filter radiation of interest upon the infrared detector 36. It is possible to dispense with the output polarizer and to utilize the angular off-axis offset of about 6 degrees from the optical axis along which the polarized interacted narrow bandwidth wavelength of interest is directed to separate the filtered signal. In this case, the infrared detector 36 would be aligned along this offset axis to receive the selected narrow bandwidth of interest.

The selected rf tuning frequency needed to select and distinguish a desired narrow bandwidth of interest for analysis is had from the relationship:

$$\lambda_0 = (V_a \Delta n / f \times (\sin^4 \theta_i + \sin^2 2\theta_i))^{\frac{1}{2}}$$

$\lambda_0$ is the wavelength of the bandwidth of interest, $V_a$ is the acoustic velocity, $\Delta n$ the birefringence, and f and rf frequency, and $\theta_i$ the angle which the incident light beam makes with the c axis or optic axis of the crystal. In setting up or aligning the system a helium neon laser of known wavelength can be directed along the optical path and rf energy of a frequency associated with the selected wavelength applied to the transducer and crystal, with the crystal being oriented to align the angle of incidence to the optic axis that gives optimal transmission of the selected wavelength of interest.

The electronic system 16 will now be described. The analog output signal from the infrared detector 36 is fed to an amplifier 38 and to analog to digital converter 40 with the resultant digital signal applied to microcomputer 42. The electrical subsystem 16 interfaces with the optical subsystem at the acousto-optical tunable filter 12 via the transducer 32 which is connected to the rf amplifier 44 from which selected frequency rf drive power is applied via the transducer 32 to launch acoustic waves in the crystal 28. In this way optically filtered infrared signals can be detected and utilized by the microcomputer to determine the absorption resulting from the presence of selected gases in this sample cell. The microcomputer 42 typically has a video output means 46 associated therewith for visual display of the detected signals, as well as memory means 48 and a printer 50. The memory means 48 stores the control and operation signals for the system. The microcomputer 42 through an appropriate interface means 52, when supplied with control signals from memory means 48, controls the output frequency and amplitude from a frequency synthesizer 54, which is connected by a gate means 56 to the rf amplifier 44 for pulse operation. The gate 56 is utilized in conjunction with a pulse inhibit circuit means 58 to provide assurance that the rf pulse of the proper width are applied to the transducer while the rf power duty cycle is limited to a load level which does not overheat the crystal. The system is thus capable of operating not only as a rapidly tunable narrow band infrared filter but also as a solid state optical chopper as well.

Control signals from memory means 48 is applied to the microcomputer 42 to sequentially apply rf pulses typically about 3.5 microseconds long at about 10 watts peak power over the operating frequency range of about 20 to 100 megahertz to the transducer of the filter. The pulses are designed to cause the filter to be transmissive at a reference wave length where there is no absorption and then at a wavelength where a known gas has a relatively strong absorbtion. In addition to rapidly sampling the absorption wavelength for a variety of gases the system is initialized with no gas present to yield the same amplitude signal as measured by the analog to digital converter for the reference wavelength and at the gas absorption wavelength. The microcomputer can then be utilized to generate feedback process control signals as a function of the analysis to control the particular process such as combustion which is being analyzed.

The system has been utilized in sampling conventional combustion product gases such as carbon dioxide which is sampled when rf frequency of 32.566 megahertz is applied and the resulting passband wavelength indicative of carbon dioxide is at 4.2 micrometers. For nitrous oxide the rf frequency is 30.395 megahertz yielding a passband wave length of 4.5 micrometers. For carbon monoxide an rf frequency of 29.101 megahertz yields a passband wavelength of 4.7 micrometers, while for methane an rf frequency of 49.335 megahertz yields a passband wavelength of 3.39 micrometers, and for sulfur dioxide an rf frequency of 18.483 megahertz yields a passband wavelength of 7.24 micrometers.

The system of the preferred embodiment is a non-collinear system where the input infrared radiation is directed at a specified angle relative to the crystal axis, which angle is selected as a function of the crystal material to achieve optimum acousto-optic interaction. Alternate embodiments can include collinear systems in which the input radiation is directed collinear with the acoustic wave propagation direction.

The system described herein is set forth in greater detail in, "Automated Acousto-Optic Tunable Filter (AOTF) Infrared Analyzer", Proceedings of SPIE, The International Society of Optical Engineering, volume 268, p. 160–166.

We claim:

1. A broadband automated acousto-optic tunable filter multigas infrared analyzer system comprising:
    (a) means for directing infrared radiation through a sample species to be analyzed, which species have predetermined infrared absorption characteristics;
    (b) means for focusing the infrared radiation after modification by the absorptive characteristics of the sample species upon said acoustic-optic tunable filter;
    (c) said acoustic-optic tunable filter comprising an input polarizer for selectively polarizing the infrared radiation directed through the sample species, and an optically aligned acousto-optic crystal through which the selectively polarized infrared radiation is passed at a predetermined angle relative to the crystal optic axis, an acoustic transducer means coupled to a variable frequency rf energy source and to the acousto-optic crystal to launch acoustic waves in the crystal to interact with a selected narrow bandwidth portion of the polarized infrared radiation to make it distinguishable from the remaining infrared radiation, which selected narrow bandwidth portion is a function of the frequency of the rf energy and acoustic waves;
    (d) infrared radiation detection means which detects the output filtered infrared radiation from the filter and generates an output electrical signal as a function of the output filtered infrared radiation;
    (e) computing means to which the detection means output electrical signal is applied for determining the species present in the sample cell, and including means for the pulsed operation of the rf energy source to determine the timing and frequency of rf energy applied to the acoustic transducer mated to the acousto-optic crystal to determine the infrared wavelength selectivity or tuning of the acousto-optic tunable filter.

2. The analyzer system set forth in claim 1, wherein the means for directing infrared radiation through a sample cell comprises a collimating mirror, which the means for focusing the collimated infrared radiation transmitted through the sample cell comprises a focusing mirror.

3. The analyzer system set forth in claim 1, wherein the acousto-optic tunable filter includes an output polarizer which is optically aligned with the input polarizer and the acousto-optic crystal, which output polarizer is oriented transversely to the input polarizer to only transmit a selected narrow bandwidth portion of the infrared radiation.

4. The analyzer system set forth in claim 3, wherein the input polarizer and the output polarizer comprise wire grid polarizers with a plurality of closely spaced parallel conductors, with the conductors of the input wire grid polarizer aligned parallel with the plane of the b-c crystalline axes of the acousto-optic crystal, and the conductors of the output polarizer are aligned transversely to those of the input polarizer.

5. The analyzer system set forth in claim 1, wherein the infrared radiation detection means comprises an infrared sensitive pyroelectric detector.

6. The analyzer system set forth in claim 1, wherein computing means includes a microprocessor and memory means for comparing the detected signal to predetermined molecular species indicative signals stored in the memory means, and wherein the memory means provides a predetermined sequence of signals which are applied to the microprocessor to be applied to a frequency synthesizer to vary the frequency of the rf energy applied to the transducer means coupled to the acousto-optic crystal to vary the selection of the narrow bandwidth portion of the infrared radiation which is analyzed, and wherein predetermined frequencies corresponding to predetermined molecular sample species are applied.

7. The analyzer system set forth in claim 1, wherein the sample species are provided in a sample cell which is disposed between the means for directing the infrared radiation and the means for focusing the infrared radiation upon the acousto-optic tunable filter.

8. The analyzer system set forth in claim 1, wherein the rf energy source includes an rf energy frequency sythesizer coupled by electronic signal gate means amplifier which is connected to the acoustic transducer, and the computing means includes a microprocessor and memory means for applying sequential pulsed control signals to the rf frequency synthesizer to predeterminedly vary the frequency of the rf energy applied to the acousto-optic tunable filter, and wherein control signals are applied to the electronic signal gate means to provide pulse width modulated rf energy to the rf amplifier.

* * * * *